(12) United States Patent
Silverton

(10) Patent No.: US 6,428,973 B1
(45) Date of Patent: *Aug. 6, 2002

(54) COMPOSITIONS AND METHODS FOR EVALUATING BONE RESORPTION

(75) Inventor: Susan F. Silverton, Ft. Washington, PA (US)

(73) Assignee: The Trustees of the University of Pennsylvania, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 47 days.

(21) Appl. No.: 09/488,758

(22) Filed: Jan. 21, 2000

Related U.S. Application Data
(60) Provisional application No. 60/117,990, filed on Feb. 1, 1999.

(51) Int. Cl.[7] .................. A61K 31/00; A61K 35/12; A61K 19/00; A61K 38/18; A61K 48/00

(52) U.S. Cl. ............... 435/29; 435/29; 435/352; 435/325; 435/6; 435/372; 514/456

(58) Field of Search ............... 514/12, 2, 8, 13, 514/14, 15, 16; 424/198; 435/6, 325, 29, 352; 530/324

(56) References Cited

U.S. PATENT DOCUMENTS
5,856,186 A * 1/1999 Rodan et al. ............... 435/372

OTHER PUBLICATIONS

Nishihara et al., "*Actinobacillus actinomycetemcomitans* Y4 capsular–polysaccharide–like polysaccharide promoets osteoclast–like cell formation by Interleukin–1alpha production in mouse marrow cultures", Infection and Immunity, vol. 63 No. 5, pp. 1893–1898, 1995.*

Akatsu, et al., "Chinese hamster ovary cells expressing Alpha–4/Beta1 Integrin stimulate osteoclast formation in vitro", Journal of Bone and Mineral Research, vol. 13 No. 8, pp. 1251–1259, 1998.*

Akatsu et al., "Chinese Hamster Ovary Cells Expressing $\alpha_4\beta_1$ Integrin Stimulate Osteoclast Formation In Vitro", *J. Bone Miner. Res.* 1998 13:1251–1259.

Bayever et al., "Human Osteoclasts Propagated from Hematopoietic Progenitors", *J. Bon Miner. Res.* 1991 6:S93.

Brown et al., "A Recombinant Murine Retrovirus for Simian Virus 40 Large T cDNA Transforms Mouse Fibroblasts to Anchorage–Independent Growth", *J. Virology* 1986 60:290–293.

Burger et al., "osteoclast Formation from mononuclear Phagocytes:Role of Bone–forming cells", *J. Cell Biol.* 1984 99:1901–1906.

Demulder et al., "Abnormalities in Osteoclast precursors and Marrow Accessory Cells in Paget's Disease*", *Endocrinology* 1993 133:1978–1982.

Hoh et al., "Atomic force microscopy for high–resolution imaging in cell biology", *Trends in Cell Biol.* 1992 2:208–213.

Jones et al., "Histomorphometry of Howship's Lacunae Formed in Vivo and in Vitro:Depths and volumes measured by scanning electron and confocal microscopy", *Bone* 1993 14:455–460.

Kurihara et al., "Osteotropic Factor Responsiveness of Highly Purified Populations of Early and Late Precursors for Human Multinucleated Cells Expressing the Osteoclast Phenotype" *J. Bone Miller. Res.* 1991 6:257–261.

Mills et al., "Multinucleated Cells Formed in Vitro From Paget's Bone Marrow Express Viral Antigens", *Bone* 1994 15:443–448.

Nishihara et al., "Actinobacillus actinomycetecomitans Y4 capsular–Polysaccharide–Like Polysaccharide promotes Osteoclast–Like Cell Formation by Interleukin–1α Production in Mouse marrow Cultures", *Infection and Immunity* 1995 63:1893–1898.

Roodman et al., "Interleukin 6 A Potential Autocrine/Paracrine Factor in Paget's Disease of Bone", *J. Clin. Invest.* 1992 89:46–52.

Shapiro et al., "Osteoclast Pit Volumes Standardized by Atomic Force Microscopy are Decreased by Ethoxzolamide", *Cell Mater* 1994 3:245–256.

Shinar et al., "The Effect of Hemopoietic Growth Factors on the Generation of Osteoclast–Like Cells in Mouse Bone Marrow Cultures", *Endocrinology* 1990 126:1728–1735.

Takahashi et al., "Role of Colongy–Stimulating Factors in Osteoclast Development", *J. Bone Miner. Res.* 1991 6:977–985.

Takahasi et al., "Osteoblastic Cells are Involved in Osteoclast Formation", *Endocrinology* 1998 123:2600–2602.

Udagawa et al., "The Bond Marrow–Derived Stromal Cell Lines MC3T3–G2/PA6 and ST2 Support Osteoclast–Like Cell Differentiation in Cocultures with Mouse Spleen Cells", *Endocrinology* 1989 125:1805–1813.

* cited by examiner

Primary Examiner—Karen Cochrane Carlson
Assistant Examiner—Patricia Robinson
(74) Attorney, Agent, or Firm—Licata & Tyrrell P.C.

(57) ABSTRACT

Compositions and methods for the evaluation of bone resorption and bone resorption-related diseases are disclosed. The compositions include a human osteoclast-like cell line capable of resorbing calcified tissue in vitro.

3 Claims, No Drawings

COMPOSITIONS AND METHODS FOR EVALUATING BONE RESORPTION

This application claims the benefit of priority from Provisional Application Ser. No. 60/117,990, filed Feb. 1, 1999.

INTRODUCTION

This invention was supported in part by funds from the U.S. Government NIH Grant No. AR40428 and the U.S. Government may therefore have certain rights in the invention.

BACKGROUND OF THE INVENTION

Bone is a dynamic tissue that remodels itself continuously by both deposition of new bone and resorption of bone cells. The cells responsible for formation of bone tissue are known as osteoblasts, while the cells involved in bone resorption are known as osteoclasts. In some situations, however, resorption of bone is increased resulting in formation of abnormal bone structure. Diseases associated with an abnormal level of bone resorption include Paget's disease, osteoporosis, and tumor-linked bone resorption disease.

Osteoclasts are located on the surface of mineralized bone. When bone is resorbed, calcium and phosphorus are released into the extracellular fluid and the organic matrix of bone is resorbed. In Paget's disease, bone resorption is usually focal. The osteoclasts in patients with Paget's disease are triggered to undergo excessive resorption which is followed by replacement of normal bone marrow with vascular, fibrous connective tissue. As the disease progresses, the resorbed bone itself is replaced by coarse-fibered, dense trabecular bone that is organized haphazardly. This haphazard bone remodeling leads to a characteristic mosaic pattern in bone rather than the organized pattern seen in healthy bone tissue. The cause of this disease is unknown and there are currently no treatments that can reverse disease and few that effectively treat this disease. There are also no animal or cellular models currently available to study the etiology or treatment of Paget's disease.

Although the exact etiology of Paget's disease is unknown, the increased osteoclast activity is considered the hallmark of the disease (Roodman, G. D. et al., *J. Clin. Invest.*, 1992, 89:46–52). Studies have shown that osteoclast number is abnormally high in active Paget's disease lesions (Mills, B. G. et al., *Bone*, 1994, 15:443–448). In addition, bone marrow accessory cells isolated from pagetic bone lesions increased the number of CD34+ colony forming units, markers for hematopoietic cells which is the cell lineage of osteoclasts, in both normal and pagetic bone marrow (Demulder, A. et al., *Endocrinology*, 1993, 133:1978–1982). These data suggest that increased bone resorption in Paget's disease is due to an increased number of osteoclasts as well as increased activity of these cells.

Information on the nature and activity of pagetic osteoclasts is limited by the difficulty of obtaining human osteoclasts from bone and by the small numbers of osteoclasts which can be obtained by in vitro bone culture methods (Demulder, A. et al., *Endocrinology*, 1993, 133:1978–1982). To date, no human cell line of osteoclasts has been established that would be useful in studying the activity of these cells in Paget's disease and well as diseases such as osteoporosis or tumor-linked bone resorption disease.

Small numbers of osteoclasts have been produced in long term bone marrow culture (Kurihara, N., C. Civin, and G. D. Roodman, *J., Bone Miner. Res.*, 1991, 6:257–261; Bayever, E. K. Haines, and S. F. Silverton, *J. Bone Miner. Res.*, 1991, 6:S93). In addition, small numbers of osteoclasts have been observed in long term culture of spleen cells along with either osteoblast or bone-derived cell lines (Takahashi, N. N. Udagawa, T. Akatsu, H. Tanaka, M. Shionome, and T. Suda, *J. Bone Miner. Res.*, 1991, 6:977–985; Takahashi, N., T. Akatsu, N. Udagawa, T. Sasaki, A. Yamaguichi, J. M. Moseley, T. J. Martin, and T. Suda, *Endocrinology*, 1988, 123:2600–2602). These multinucleate tartrate-resistant acid phosphatase-positive cells have several characteristics which resemble an isolated osteoclast, including the ability to form resorption pits in calcified tissue. However, these cell lines which appear to generate osteoclast cells required more than one cell type to produce the bone-resorbing cells (Takahashi, N., T. Akatsu, N. Udagawa, T. Sasaki, A. Yamaguichi, J. M. Moseley, T. J. Martin, and T. Suda, *Endocrinology*, 1988, 123:2600–2602; Burger, E. H., J. W. M. van der Meer, and P. J. Nijweide, *J. Cell Biol.*, 1984, 99:1901–1906; Udagawa, N., N. Takahashi, T. Akatsu, T. Sasaki, A. Yamaguichi, H. ,Kodama, T. J. Martin, and T. Suda, *Endocrinology*, 1989, 125:1805–1813; Shinar, D. M., M. Sato, and G. A. Rodan, *Endocrinology*, 1990, 126:1728–1735). These cell line data suggested that cell to cell contact between an osteoclast precursor and the support cell was required for development of cells with osteoclast activity, i.e., bone resorptive capacity. None of this research, however, has demonstrated the production of a human cell line of osteoclast or osteoclast-like cells that is derived solely from one cell type.

When osteoclast-like cells are obtained by either isolation from human bone or in vitro cell culture, a functional characterization is required to differentiate osteoclasts from closely related macrophages or giant cells. Osteoclasts, but not other cells, are able to excavate focal areas of a calcified substrate when they are adherent to the calcified substrate (Jones, S. J. and A. Boyde, *Bone*, 1993, 14:455–460). Confirmation of this focal resorptive capacity requires analysis of calcified tissue destruction as evidenced by increase in pit number, pit area, and pit volume in the calcified substrate.

The present invention provides an osteoclast-like human cell line using bone cells from Paget's patients.

SUMMARY OF THE INVENTION

An object of the present invention is to provide a human osteoclast-like cell line wherein the cell line is capable of resorbing calcified tissue in vitro.

Another object of the present invention is to provide a method for screening agents for treatment of bone resorption-related diseases comprising establishing a human osteoclast-like cell line which is adherent to a sample of calcified tissue, contacting the cell line with an agent to be screened, and determining whether the agent decreases resorption of the calcified tissue sample. Also claimed are methods for screening agents for treatment of the specific diseases associated with increased bone resorption that includes Paget's disease, osteoporosis, and tumor-linked bone resorption disease.

Yet another object of the present invention is to provide an in vitro model for Paget's disease of bone.

DETAILED DESCRIPTION OF THE INVENTION

The present invention is a human "osteoclast-like" cell line. "Osteoclast-like" cells are cells of a single type that were derived from pagetic bone tissue and have the ability to cause resorption of calcified tissue in vitro. These cells provide an in vitro model for Pagent's disease.

Cells were transformed from pagetic bone using large "T" antigen and the immortalized cell line of the present invention was created. The cell line was shown to have the capacity to resorb calcified tissue, the unique characteristic of these cells, by culturing the cell lines on coverslips and dentin slices (the calcified tissue source). In addition to carrying out focal resorption of calcified tissue in vitro, these cell lines express colony stimulating factors such as M-CSF and G-CSF, and have the presence of other osteoclast markers including tartrate resistance acid phosphatase and carbonic anhydrase. In addition, these cell lines are able to support the development of osteoclasts from normal bone marrow in vitro.

Human pagetic bone tissue was removed during osteotomy to correct a significant bone defect caused by long-standing Paget's disease of bone. The cells were prepared for culture and transfection. Cells were infected with a retrovirus containing the coding sequence for SV40 T antigen packaged in the PA317 cell line. The human pagetic cells were then grown and maintained and passaged continuously every 3 weeks. After 18 months, all cell lines increased their proliferative rate significantly and were then passaged once a week.

The characteristics of the cells were then determined. Expression of T antigen was assayed by immunofluorescence. Expression of CD34 antigen was assayed with a monoclonal antibody against human CD34 conjugated to fluorescein. The cell lines were positive for both antigens, consistent with osteoclast cells that had been transfected with T antigen.

Cell morphology was consistent with that of osteoclasts. Both pyramidal and round cells were seen in all cultures, at a ratio of about 20:1. All cells were grown on glass coverslips in the presence of a dentin (calcified tissue) disc. When adherent to the dentin discs, these pagetic cell lines were positive for osteoclast markers such as tartrate-resistant acid phosphatase, carbonic anhydrase, and succinic dehydrogenase. Some cells were positive for the vitronectin receptor. The cells lines were also shown to express M-CSF and G-CSF but not GM-CSF, IL-6 or TNF-alpha.

After all assays were performed for analysis of markers in the cell lines, the dentin slices were removed from culture and washed for resorption pit analysis. The pits were visualized with Toluidine Blue stain and the defects created by the cells were observed and counted using either light microscopy or scanning electron microscopy.

At a seeding density of $2 \times 10^4$, pagetic cell lines showed pit densities with a range of 2–68 and a median of 10 pits per $0.2$ cm$^2$ after 7–10 days. Pit areas were widely distributed. Pit depths, standardized by atomic force microscopy, ranged from 0.03 to 0.9 microns, with a median of 0.27 microns. Pit volumes ranged from 5 to 1141 cubic microns.

Pagetic cell lines were also co-cultured with adherent human bone marrow cells. Bone marrow cells had been collected after informed consent during bone marrow harvesting in normal subjects for bone marrow transplantation. These bone marrow cells were also plated in wells containing a dentin slice and cultured before addition of cells from the pagetic cell lines. After co-culture, the number of tartrate-resistant acid phosphatase cells was determined. The number of these marker cells increased with co-culture as compared to culture of bone marrow cells without pagetic cell lines added. This is the first demonstration of such an effect in a human osteoclast-like cell line. The immortalized cells demonstrated the capacity to increase the yield of bone resorptive cells from undifferentiated normal bone marrow. Such an effect is characteristic of pagetic cells and may explain in part the increased resorptive capacity that is typically seen in this disease.

The cell lines of the present invention are the first human osteoclast-like cell lines characterized and shown to have the ability to induce bone resorption in calcified tissue. The cell lines of the present invention are useful in the study of Paget's disease and for screening agents that might be active to decrease the bone resorptive capacity of osteoclasts in this disease. The cell lines are also useful in the study of other diseases characterized by increased bone resorption, also termed bone resorption-related diseases, such as osteoporosis and tumor-linked bone resorption disease, or any condition where the activity of osteoclasts has been implicated.

Another embodiment of the present invention is a screening assay for agents to be tested for the treatment of a bone resorption-related disease. The diseases include Paget's disease, osteoporosis, and tumor-linked bone resorption disease. In this screening assay, an osteoclast-like cell line of the present invention is established that is adherent to a sample of calcified tissue, for example a dentin slice. Then the cell line is contacted with an agent to be screened for treatment of a bone resorption-related disease. The endpoint to be determined in the assay is whether the test agent affects the resorption of calcified tissue in vitro, when compared to resorption in cell lines without addition of the test agent. Agents that would be useful in the treatment of such bone resorption-related diseases would decrease the level of bone resorption in the calcified tissue. Bone resorption can be measured by methods well known to those of skill in the art, including a pit assay using microscopic examination of pits on the calcified tissue sample. Levels of test agents to test in the screening assay would be chosen based on the knowledge of one of skill in the art of in vitro drug screening. Such doses typically range from $10^{-9}$ M to $10^{-4}$ M.

The following nonlimiting examples are provided to further illustrate the present invention.

EXAMPLES

Example 1

Isolation of Bone Cells

Informed consent was obtained from the patient. A bone wedge was removed from a patient with long-standing Paget's disease during osteotomy. The bone wedge was removed aseptically and immediately transferred to ice-cold α-MEM (Sigma Chemical Co.) Containing 200 units/L heparin. The bone was minced into small fragments and transferred into sterile 50 ml tubes. The fragments were incubated sequentially in collagenase (125 units/ml) and trypsin (0.025%) for 15 minutes at 37° C., then shaken vigorously in α-MEM for 4 minutes to dislodge the cells. The cell suspension was decanted, saved and fresh medium added. The digestion and shaking steps were repeated 3 times. The cells were filtered through a Nytex 350/36 mesh, centrifuged at 1500 rpm for 5 minutes and resuspended in α-MEM containing 10% Fetal Bovine Serum, 10 units penicillin and 10 μg streptomycin per ml. The total cell yield was $5.5 \times 10^7$.

Example 2

Transfection of Bone Cells

For the transfection/infection procedure, $5 \times 10^5$ cells were plated per 35 mm dish and incubated at 37° C. and 5% $CO_2$ for 24 hours. One aliquot of cells was incubated with ZIPTEX, a retrovirus containing the coding sequence for SV40 T antigen (Brown, M. et al., *J. Virology*, 1986, 60:290–293) packaged in the PA317 cell line (Miller, A. D. et al., *Mol. Cell. Biol.*, 1986, 6:2895–2902). The cells were infected overnight in the presence of 8 µg/ml polybrene. A second aliquot was transfected with pSV3B containing the entire SV40 viral sequence, using a calcium phosphate transfection kit (FIVE PRIME THREE PRIME).

The human pagetic cells grew slowly during the initial 24–48 passages. All were maintained in α-MEM (10% Fetal Bovine Serum with 10 units penicillin and 10 µg streptomycin per ml) and passaged continuously approximately every 3 weeks, at a ratio of 1:2. Approximately 18 months after infection and transfection, the cell line increased proliferative rate significantly. Thereafter, cells were passaged once a week. The increased proliferative rate has continued through all succeeding passages.

Examples 3
Growth of Osteoclast-Like Cells

All cells were grown on glass coverslips in the presence of a dentin disc. The dentin discs were prepared from polished cross sections of human premolars. The teeth were cut with a low speed saw and a diamond blade. The discs were examined for defects and comparable cross sectional areas were cut with surgical scissors. The average area of discs was 0.2 cm². Dentin discs were calcified in a calcium phosphate solution (2 mM $CaCl_2$ mixed with 2 mM $Na_2HPO_4$, final pH of 6.93) at 4° C. for 3 weeks. When viewed by scanning electron microscopy, the overcalcified surface was a series of plate-like calcium phosphate deposits with a Ca/P ratio of 0.88 by elemental analysis.

Example 4
Immunofluorescence of T Antigen

Expression of SV40 T antigen was assayed by immunofluorescence. Cells grown on coverslips as described above were fixed with cold methanol for 10 minutes at –20° C., blocked with normal goat serum (20 minutes) and incubated with a monoclonal antibody Ab-2 against T antigen (Oncogene Science) for 60 minutes at a concentration of 1:20. After 3 washes with PBS buffer, the cells were incubated with FITC labeled anti-mouse secondary antibody (Organon Teknica) for 45 minutes at 1:20. Controls were not incubated with Ab-2.

Example 5
Immunofluorescence of CD34 Antigen

Cells were fixed with 4% paraformaldehyde for 10 minutes at room temperature. The coverslips were washed with PBS buffer, blocked with 1% PBS buffer for 30 minutes, and incubated overnight at 4° C. with a monoclonal antibody against human CD34 conjugated to fluorescein (Research Diagnostics Inc.) at a concentration of 1:25. They were washed with distilled water and mounted in glycerol. Control cells were the PSV-10 cell line, a CD34 negative pagetic cell line.

Example 6
Immunocytochemistry for Osteoclast Markers

All cells were grown on glass coverslips in the presence of a dentin disc as described above. The cells were rinsed once with warm CMF (calcium, magnesium-free) buffer, fixed for 10 minutes in 70% ethanol at room temperature, then rinsed again with PBS buffer at pH 7.4. The coverslips and dentin were then incubated in blocking serum for 15–30 minutes (1% BSA, 5% rat serum, 1% BSA, respectively), washed with PBS buffer and incubated with primary antibody for 1 hour at room temperature. For each marker the dilutions were: sheep anti-human carbonic anhydrase II, 1:200; mouse anti-human $\alpha_V\beta_3$ vitronectin, 1:100; and sheep anti-human alkaline phosphatase, 1:100. They were then rinsed with PBS buffer three times (10 minutes each) and incubated with horseradish peroxidase-labeled secondary antibody for 1 hour at room temperature. For each marker these were: donkey anti-sheep IgG, 1:200; sheep anti-mouse IgG, 1:100; and donkey anti-sheep IgG, 1:100. After 3 washes with PBS buffer, the cells were reacted with a DAB solution (0.5 mg/ml DAB in PBS and 10 µl 3% $H_2O_2$) for 10 minutes. The reaction was stopped with a distilled water rinse. Dentin slices and coverslips were mounted in glycerol for observation. Controls were not exposed to the respective primary antibodies.

Example 7
Succinate Dehydrogenase Staining

The cells on dentin and coverslips were washed with warm CMF buffer and fixed in 70% ethanol for 10 minutes at room temperature. The cells were rinsed with distilled water, freeze-thawed to allow penetration of the succinic acid into the mitochondria and incubated in 250 mM sodium phosphate buffer containing 100 mM succinic acid, 0.032 g/ml nitrobluetetrazolium, 0.5 mg/ml NAD, at pH 7.4, for 30 minutes at 37° C. The cells were rinsed with distilled water and mounted. Controls had no succinic acid added.

Example 8
Tartrate-Resistant Acid Phosphatase

The adherent cells or substrate and coverslip were washed with warm CMF buffer, then fixed and stained for tartrate resistant acid phosphatase with a Sigma Leukocyte Acid Phosphatase Kit (Sigma) for 15–30 minutes. Positive cells were observed under a light microscope. Control cells had no substrate solution added.

Example 9
PCR Analysis for Expression of Cytokine mRNAs by Paget's Cell Lines

Total RNAs were extracted from $10^6$ Paget's cell lines by the guanidine thiocyanate-CsCl method with some modification. Oligonucleotides specific for beta-actin or various cytokines were purchased from Genosys (Woodlands, Tex.) or from Stratgene (La Jolla, Calif.). RT-PCR was performed using a GeneAmp RNA/PCR kit (Perkin-Elmer Cetus, Norwalk, Conn.) with a Perkin-Elmer Cetus DNA thermal cycler according to the manufacturer's protocol for RT/PCR. Briefly, RNA primed with random primers was reverse transcribed using cloned Moloney Leukemia virus reverse transcriptase (2.5 U), 1 mM of each deoxy-NTP, 50 pmole random hexamer, 1 U RNAse inhibitor, in a final volume of 20 ml. The reaction was run at room temperature for 10 minutes followed by raising the temperature to 42° C. for 30 minutes to complete the extension reaction. The reaction was heated to 95° C. for 5 minutes to denature the RNA-cDNA hybrids and quick-chilled on ice. PCR was performed with Taq DNA polymerase with 20 pmole of appropriate primers for each cytokine. The cycle profile was as follows: 45 seconds at 94° C. for denaturation, 1 minute 30 seconds at 60° C. for primer annealing, and 2 minutes at 72° C. for primer extension for 45 cycles, then finally a 10 minute extension at 72° C. PCR products were electrophoresed in 1.5% agarose gel and visualized using ethidium bromide staining.

Example 10
Co-culture with Adherent Human Bone Marrow Cells

Bone marrow was collected after informed consent during bone marrow harvesting in normal subjects for bone marrow transplantation. Bone marrow was collected in cold CMF (Hanks Basic Salt Solution without calcium or magnesium). The bone marrow solution was diluted 1:2 in additional CMF and layered over Ficoll-Hypaque (5 ml bone marrow solution to 3 ml Ficoll-Hypaque). The layers were centrifuged at 1500 rpm for 30 minutes at room temperature. The mononuclear cell layer was removed from the liquid interface, placed in ice cold CMF and diluted to 15 ml. The solution was centrifuged at 1500 rpm for 10 minutes and the cell pellet harvested and diluted with 1 ml DMEM with 10% Fetal Calf Serum. The cells were plated at a density of $2\times10^5$ into 1 ml wells containing a dentin slice and a coverslip and cultured for 7 days. A mesh disc was then placed over the cells and dentin and $1\times10^4$ immortalized pagetic cells were added to the well. The mesh was 0.4 μm pore size to prevent cell migration. After 5 days, coverslips and dentin slices were fixed and stained for tartrate resistant acid phosphatase. Cell numbers on coverslips and dentin were also counted.

After co-culture, the number of tartrate-resistant acid phosphatase cells increased as compared to culture of bone marrow cells without pagetic cell lines added. Without addition of the immortalized pagetic cells, the number of tartrate-resistant acid phosphatase cells on dentin ranged from 4–10, with a median of 4. When cultured with immortalized pagetic cells but separated by a membrane, the cell number on dentin ranged from 6–95, with a median of 24, a significant increase (p<0.005). Therefore, the immortalized cells demonstrated the capacity to increase the yield of bone resorptive cells from undifferentiated normal bone marrow.

Example 11
Resorption Pit Assay and Analysis

The dentin slices were washed with 1% Triton X-100 detergent and rinsed with distilled water. The substrate was sonicated in distilled water for 10 minutes, submerged in Toluidine Blue for 5 minutes and washed in 3 changes of distilled water to remove excess stain. The defects created by the osteoclast-like cells were observed and counted using either light microscopy or scanning electron microscopy (SEM).

Discs were dehydrated by graded alcohols and prepared for SEM by evaporation of Freon 113. Critical point drying was not utilized for these hard tissue samples. The SEM used for these studies was a JEOL JSM T330A. Stereopair photographs were taken of pits for each group. The pictures were taken at angles of +7 and -7 degrees. The tilt stage was within 0.5 degrees. Pits were present on each slice. Steropairs were viewed under the stereoscope and the 3-dimensional images evaluated for depth. Each pit was then analyzed individually to decide the number of surfaces to be measured as part of the volume calculations. To measure the surface areas associated with the pits, the photographs were xerographed with enlargement and the surfaces predetermined from the 3-dimensional morphology were traced on the xerograph, cut out and weighed. Standard square micron areas were determined by using the micron bar from the SEM after appropriate standardization with a 10 micron grid at all pertinent magnifications.

For stereoscope depth analysis, the depth was determined on preselected surfaces. A red dot is present on the depth detection lens for each eye. As the micrometer screw is rotated, the dots move physically apart. The eye however, creates an optical illusion that the two dots are one and that they are descending into the put. The micrometer screw is used to measure the distance that the dot "falls". In other experiments, half of the pits had depths measured by 2 observers, with a variation between observers of only 6%.

To standardize the depth measurement, Atomic Force Microscopy (AFM) and 3D reconstruction of the pit depths was carried out on a selected pit of medium depth and symmetrical morphology (Shapiro, M. et al., *Cell Mater,* 1994, 3:245–256; Hoh, J. H. and P. K. Hansmal, *Trends Cell Biol.,* 1992, 2:208–213). The AFM used was a Digital Instruments Dimension 3000 and used a pyramidal cantilever tip in tapping mode. The dimensions of the tip were from 5–50 nm. The AFM depth measurement was standardized using precision mica profiles. Edge artifacts on osteoclast pits by AFM are apparently common, due to the undercutting of the surface of cells during resorption and the physical shape of the cantilever apparatus of the microscope (Shapiro, M. et al., *Cell Mater.,* 1994, 3:245–256). As the pits seen were relatively shallow, minimal undercutting was seen. The pit depth was then able to be reproducibly determined in microns. The pit depths by AFM were averaged and used to calculate the volume of the standard pit and to compare the micrometer screw readings of the stereoscope to AFM depths.

At a seeding density of $2\times10^4$, pagetic cell lines showed pit densities with a range of 2–68 and a median of 10 pits per $0.2 \text{ cm}^2$ after 7–10 days. Pit areas were widely distributed with a range of 105–3575 square microns. The median area was 706 square microns. Pit depths, standardized by atomic force microscopy, ranged from 0.03 to 0.9 microns, with a median of 0.27 microns. Pit volumes ranged from 5 to 1141 cubic microns with a median of 123 cubic microns.

What is claimed is:

1. An immortalized human osteoclast-like cell line derived from bone-related diseased human tissue with increased osteoclastic activity which cell line resorbs calcified tissue in vitro.

2. A method of screening agents for treatment of a bone resorption-related disease comprising:
   (a) establishing the cell line of claim 1 adherent to a sample of calcified tissue;
   (b) contacting said cell line with an agent to be screened for treatment of a bone resorption-related disease;
   (c) determining whether said agent decreases the resorption of said calcified tissue in vitro.

3. The method of claim 2 wherein the bone-related disease is Paget's disease, osteoporosis, or tumor-linked bone resorption disease.

* * * * *